United States Patent
Castellini

(10) Patent No.: US 6,612,838 B2
(45) Date of Patent: Sep. 2, 2003

(54) METHOD FOR STERILIZING CONDUITS THAT CONVEY FLUID TO MEDICAL INSTRUMENTS, ESPECIALLY DENTAL INSTRUMENTS

(75) Inventor: Franco Castellini, Bologna (IT)

(73) Assignee: Castellini S.p.A., Bologna (IT)

( * ) Notice: Subject to any disclaimer, the term of this patent is extended or adjusted under 35 U.S.C. 154(b) by 0 days.

(21) Appl. No.: 09/872,660

(22) Filed: Jun. 1, 2001

(65) Prior Publication Data

US 2001/0051325 A1 Dec. 13, 2001

(30) Foreign Application Priority Data

Jun. 9, 2000 (IT) ................................. BO2000A0345

(51) Int. Cl.[7] .............................................. A61C 19/00
(52) U.S. Cl. ........................................ 433/80; 433/82
(58) Field of Search ..................... 433/80, 82; 422/28; 210/764

(56) References Cited

U.S. PATENT DOCUMENTS

| 4,971,765 A | * | 11/1990 | Loretti et al. | ............... 141/236 |
| 5,785,523 A | * | 7/1998 | Overmyer | ................. 422/28 |
| 6,250,920 B1 | * | 6/2001 | Overmyer | ................. 433/80 |

FOREIGN PATENT DOCUMENTS

| DE | 3028550 | | 2/1982 |
| DE | 3611329 | | 10/1987 |
| EP | 0 111 249 B1 | | 5/1989 |
| EP | 0 317 521 A2 | | 5/1989 |
| EP | 0 317 521 B | | 9/1991 |
| EP | 0 734 692 A3 | | 2/1996 |
| EP | 0 734 692 A2 | | 2/1996 |
| IT | 0403442 A2 | * | 12/1990 |
| WO | WO 95/20366 | | 3/1995 |

* cited by examiner

Primary Examiner—Kevin Shaver
Assistant Examiner—Melba Bumgarner
(74) Attorney, Agent, or Firm—Fay, Sharpe, Fagan, Minnich & McKee, LLP

(57) ABSTRACT

A method for sterilizing conduits that convey fluid from a main water source to medical instruments, especially dental handpieces includes removing at least the end portions of supply branches of the handpieces from their respective rest positions and placing them in a container. A disinfectant liquid is introduced into each of the supply branches for a predetermined time. The sterilization liquid is drained out of the supply branches by flushing the inside of the supply branches with a sterile fluid supplied through a second branch independent of the main water source.

20 Claims, 1 Drawing Sheet

METHOD FOR STERILIZING CONDUITS THAT CONVEY FLUID TO MEDICAL INSTRUMENTS, ESPECIALLY DENTAL INSTRUMENTS

BACKGROUND OF THE INVENTION

The present invention relates to a method for sterilizing conduits that convey fluid to medical instruments, especially dental instruments.

It is known that the heart of any piece of dental apparatus or equipment is the water and air system. In the system, the water line supplies fluids used by dental equipment and patients (water or physiological saline for tumblers and handpieces), or consumer units (swilling water for the spittoon), while the air line is used for certain items of equipment (air spray handpieces, cooling air and driving air).

With increases in general standards of hygiene and in the "fragility" of dental apparatus and equipment, several advances have been made in the design and function of the fluid systems of dental units not only to guarantee their efficient operation and durability but also to maintain the sterility of the conduits both during and after successive patient treatments. Considering that the basic structure of such fluid systems comprises a first main line supplying water from the mains, and a second main line supplying air from an external source (compressor), each of which has a plurality of branches serving the water- or air-using devices, different systems have been designed on the basis of different methods aimed at improving the functioning and disinfection of these fluid lines or parts of them.

In particular, the present specification focuses attention on the water line which is disinfected according to two different methods, one using a continuous cycle and the other a discontinuous cycle, and requiring additional devices to be fitted to the basic structure of the system: in U.S. Pat. Nos. DE-3.028.550 and DE-3.611.329, the problem is addressed using equipment comprising a tank of disinfectant connected to a unit for dosing the disinfectant into the conduits that convey the fluid to the devices of the dental unit, in such a way as to supply the water line with disinfected water according to the amount of water required by the devices themselves.

On the other hand, in the solutions based on the discontinuous disinfection/sterilization cycle, as disclosed in patent publications EP-111.249 and EP-317.521 (the latter being by the present Applicant), the mains water supply is shut off, and a dedicated branch equipped with an independent tank is used to feed sterilizing liquid into the conduits that supply water to the handpieces. After a preset time, depending on the quality of disinfection/sterilization required and the properties of the sterilizing liquid, the line is opened again and the sterilizing liquid drained out.

The drainage of the sterilizing liquid is performed by flushing water supplied by the main line and opening the control valves on the handpieces so that the water rinses the water line and flows out into an appropriate drain.

This method, which has been used on dental units for some time, has proved to be very effective and practical. However, the Applicant, always seeking to improve the sterilization and post-sterilization steps of dental units, has made significant changes to the sterilization method in an attempt to make it safer still, in particular by improving the disinfection level of the step of draining the sterilizing liquid out of the line. This is because it has been found that the flow of non-sterile water from the main water source makes it impossible to maintain the sterility of the conduits, thus partly offsetting the sanitizing effect of the sterilizing liquid.

This sterilization parameter is very important when it is necessary to use physiological saline for a treatment on a patient. In such a case, the saline is conveyed along conduits that are not completely sterile, thus greatly diminishing the effect of the sterilizing cycle previously carried out.

SUMMARY OF THE INVENTION

The aim of the present invention, therefore, is to maintain the conduits of the dental unit water lines at the highest possible level of sterility.

Accordingly, the invention, as disclosed in the claims below, provides a method for sterilizing the conduits that convey fluid to medical instruments, especially dental handpieces and comprising the following steps: removing at least the end portions of supply branches or forks of the handpieces from their respective rest positions and placing them in a container; introducing a sterilizing liquid in each of the supply branches or forks for a predetermined time; and draining the sterilizing liquid out of the branches or forks; the final draining step is effected by flushing the branches or forks with a sterile fluid that can be supplied through a second branch independent of the main water source.

BRIEF DESCRIPTION OF THE DRAWINGS

The technical features of the present invention, in accordance with the above-mentioned aims, are set out in the claims below and the advantages more clearly illustrated in the detailed description which follows, with reference to the accompanying drawing, which illustrates a preferred embodiment of the invention without restricting the scope of the inventive concept, and in which:

DESCRIPTION OF THE PREFERRED EMBODIMENTS

Figure 1:
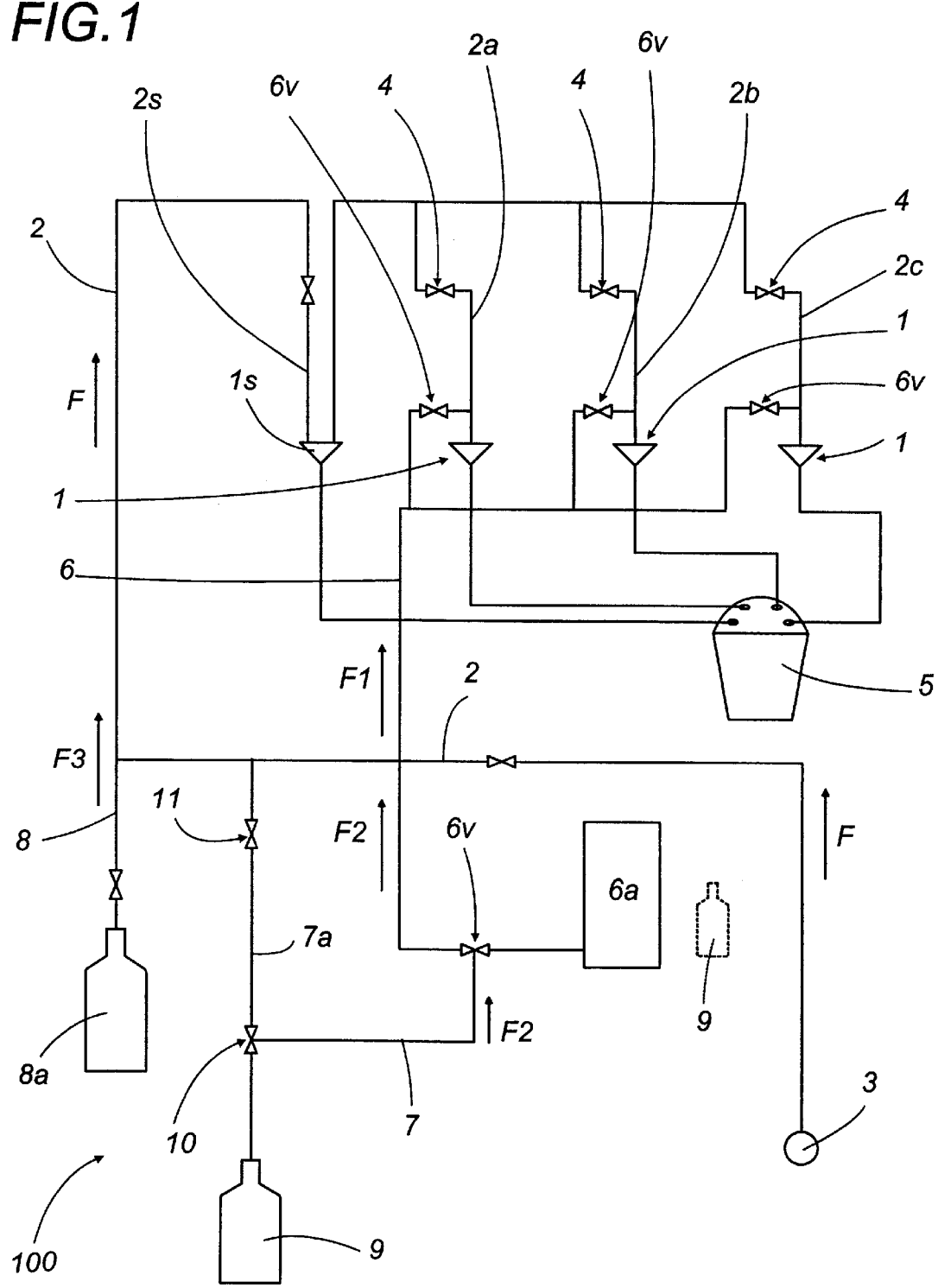
FIG. 1 is a diagram of a part of the water system of a dental unit where the method according to the present invention can be implemented.

With reference to the accompanying drawing, the method according to the invention is used to sterilize/disinfect the conduits that convey fluids to medical instruments, especially handpieces forming part of a dental unit.

The handpieces are generically denoted by the numeral 1 and not illustrated in detail since they are of very well known type. They include a micromotor, a turbine, a scalpel, a scaler, a syringe (labeled 1s), etc.

The dental unit also comprises a line 2 that supplies a fluid (water) from a main water source 3, the water line 2 subdividing into several branches or forks 2s, 2a, 2b, 2c, each corresponding to a handpiece 1 forming part of the dental unit and requiring the fluid for its operation.

Each branch 2s, 2a, 2b, 2c is equipped with first shutoff means 4, consisting of a valve, that permits the fluid to be supplied when required.

The method illustrated in FIG. 1 is represented through a circuit structure consisting of different lines, corresponding to different steps, with reference to patent EP-317.521 by the present Applicant, but without restricting the scope of the inventive concept, which may also apply to a circuit structure that is more or less complex than the one illustrated.

The method essentially comprises the following steps at least:

removing at least the end portions of supply branches or forks 2s, 2a, 2b and 2c from their respective rest positions and placing them in a container 5;

introducing a disinfectant/sterilizing liquid in each of the branches 2s, 2a, 2b and 2c of the water line 2 through (in the embodiment illustrated) a first branch 6, equipped with a valve 6v, independent of the water line 2 and leading at least into the branches 2a, 2b and 2c (see arrow F1) or flowing into the line itself;

draining the disinfectant/sterilizing liquid at least out of the branches 2a, 2b and 2c of the water line 2 through the handpieces 1 and into the container 5.

The step of draining the disinfectant/sterilizing liquid is performed by flushing the water line and the branches 2a, 2b and 2c of the water line 2 with a sterile fluid that can be supplied by the first branch 6 itself or, preferably, by a second branch 7 (see arrow F2) which is independent of the first branch 6 and of the main water source 3.

As shown in FIG. 1, the method, in this particular embodiment, also comprises a step of closing the first shutoff means 4, thus isolating the branches 2a, 2b and 2c of the water line 2 at least at the shutoff means 4 (that is, downstream of these branches relative to the supply flow direction F) before the step of introducing the disinfectant/sterilizing liquid.

Preferably, the step of flushing with the sterile fluid is at least long enough to allow the disinfectant/sterilizing liquid to drain out and the entire water line 2 (besides the branches 2s, 2a, 2b and 2c) which has come into contact with the disinfectant/sterilizing liquid to be completely rinsed and flushed through the handpieces 1 located in the container 5.

After flushing the disinfectant/sterilizing liquid out of the line 2, the user fluid can be supplied by the main water source 3 again, thus causing the sterile fluid to flow out and reopening the shutoff means 4 (in the specific embodiment illustrated).

Alternatively, the method may comprise a step of supplying physiological saline, instead of the fluid supplied by the main circuit 3 and the sterile fluid, through a third branch 8, independent of the others, equipped with a third tank 8a and connected to the water line 2, which enables the sterile fluid to flow out and remains in the water line 2 so that it can be used during treatment of a patient (see arrow F3).

In another, simpler embodiment, the first branch 6 or the second branch 7 keeps the line 2 supplied with sterile fluid which can be used during treatment. This may be achieved by providing the branch 7 with a sub-branch 7a leading upstream of the first branch 6—again relative to the flow F and in the embodiment illustrated, with an independent tank—from where the disinfectant/sterilizing liquid comes or connected directly to the first branch 6: in this way, after the step of draining out the disinfectant/sterilizing liquid and closing the first branch 6, the sub-branch 7a is opened to allow the sterile fluid to flow continuously into the water line 2.

As shown in FIG. 1, the sterile fluid is supplied by a second tank 9 placed on the dental unit. The tank 9 may be removed from the dental unit, sterilized and the liquid inside it changed or it may itself be changed if it is of the disposable type.

The dental unit, labeled 100, that implements the above described method accordingly comprises at least one first branch 6, independent and flowing into the water line 2 and at least into its branches 2a, 2b, 2c. The first branch 6 can, when necessary and through second shutoff means 6v, supply the disinfectant/sterilizing liquid drawn from a first tank 6a, and after the first tank 6a is substituted with the second, removable tank 9 (see dashed line in FIG. 1) which is interchangeable and/or sterilizable, it may supply the aforementioned sterile flushing fluid that may also be used as an alternative fluid during a treatment session.

Alternatively, the dental unit 100 may comprise a second branch 7, parallel to the first branch 6, equipped with the second tank 9 of sterile fluid (that may be fitted without removing the first tank 6a of disinfectant/sterilizing liquid), and supplying the first branch 6 downstream of the first tank 6a through corresponding third shutoff means 10 so as to completely flush the disinfectant/sterilizing liquid out of the water line 2.

The second branch 7 is supplied by the second tank 9 containing the sterile fluid, placed directly on the dental unit 100 and being preferably of the removable, disposable type, or sterilizable if it is not disposable.

The second branch 7 may be equipped with a sub-branch 7a leading to a point upstream of the confluence between the first branch 6 and the water line 2 and the branches 2s, 2a, 2b and 2c, and able to be activated through a valve 11 in such a way as to flush the water line and make the sterile fluid available for a treatment session.

The accompanying drawing also shows a third tank 8a containing physiological saline to supply the aforementioned third branch 8 flowing into the water line 2 instead of the sterile fluid. Obviously, since the tanks are removable and of the disposable or sterilizable type, the third tank 8a may be fitted in one of the two branches 6 or 7 (in place of the first or second tank 6a or 9) without restricting the scope of the inventive concept.

In all the configurations described, after the water lines have been sterilized, the sterile fluid used to flush the lines can be used immediately to supply the spray handpieces 1 during the treatment of a patient, thus enabling the sterile fluid to be conveyed along a perfectly sterilized line.

The method thus devised achieves the preset aims thanks to a simple change in the step of draining out or flushing the sterilizing liquid performed by introducing a sterile fluid in the supply circuit just sterilized so as to maintain the water line and the fluid subsequently used during treatment at a high level of sterility.

Advantageously, the sterile fluid may be used for the treatment session or it may be substituted by physiological saline or by the fluid from the main water source.

This change in the method involves few changes to the dental unit: at most, the addition of another branch which is used to supply the sterile fluid, and which does not alter the basic structure of the dental unit.

The invention described can be subject to numerous modifications and variations without thereby departing from the scope of the inventive concept. Moreover, all the details of the invention may be substituted by technically equivalent elements.

What is claimed:

1. A method for sterilizing or disinfecting conduits that convey fluid to handpieces of a dental unit of the type comprising:
   (i) a water line which supplies a fluid from a main water source through supply branches; and,
   (ii) shutoff means for each handpiece;
   the method comprising:
      removing at least end portions of the supply branches from their respective rest positions and placing them in a container;
      introducing at least one of a disinfectant liquid and sterilizing liquid in each of the supply branches for a predetermined time;
      draining the at least one of the disinfectant liquid and sterilizing liquid out of the supply branches through the handpieces respectively connected to the supply branches, said step of draining comprising flushing the supply branches with a sterile fluid supplied through a branch that is independent of the main water source.

2. The method according to claim 1, wherein the step of flushing the supply branches with sterile fluid is at least long enough to allow the at least one of the disinfectant liquid and sterilizing liquid in the supply branches to drain out of the supply branches completely.

3. The method according to claim 2, wherein:
the step of removing the end portions of the supply branches from their respective rest positions is followed by a step of closing the shutoff means for each handpiece to isolate a portion of each supply branch located downstream from each shutoff means;
the step of introducing the at least one of the disinfectant liquid and the sterilizing liquid comprises introducing the at least one of the disinfectant liquid and the sterilizing liquid into the isolated portion of each supply branch through a first branch that is independent of the supply branches and that flows into each supply branch at a point downstream of each shutoff means; and,
said step of draining the at least one of the disinfectant liquid and the sterilizing liquid out of the supply branches comprises supplying said sterile fluid to said supply branches through a second branch that is independent of the first branch and independent of the main water source.

4. The method according to claim 2, further comprising:
supplying user fluid from the main water source to the supply branches after said supply branches are flushed with said sterile fluid from said second branch.

5. The method according to claim 2, further comprising:
supplying a physiological saline fluid into the supply branches after said supply branches are flushed with said sterile fluid.

6. The method according to claim 1, wherein:
the step of removing the end portions of the supply branches from their respective rest positions is followed by a step of closing the shutoff means for each handpiece to isolate a portion of each supply branch located downstream from each shutoff means;
the step of introducing the at least one of the disinfectant liquid and sterilizing liquid comprises introducing the at least one of the disinfectant liquid and sterilizing liquid into the isolated portion of each supply branch through a first branch that is independent of the supply branches and that flows into each supply branch at a point downstream of each shutoff means; and,
said step of draining the at least one of the disinfectant liquid and sterilizing liquid out of the supply branches comprises supplying said sterile fluid to said supply branches through a second branch that is independent of the first branch and independent of the main water source.

7. The method according to claim 6, further comprising:
supplying user fluid from the main water source to the supply branches after said supply branches are flushed with said sterile fluid from said second branch.

8. The method according to claim 6, further comprising:
supplying a physiological saline fluid from a third, independent branch that is connected to the supply branches after said supply branches are flushed with said sterile fluid.

9. The method according to claim 1, further comprising:
supplying user fluid from the main water source to the supply branches after said supply branches are flushed with said sterile fluid from said second branch.

10. The method according to claim 1, further comprising:
supplying a physiological saline fluid into the supply branches after said supply branches are flushed with said sterile fluid.

11. The method according to claim 1 wherein the step of flushing the supply branches with sterile fluid comprises drawing the sterile fluid from a tank that is removably positioned on the dental unit.

12. The method according to claim 1, further comprising:
using the sterile fluid flushed through the supply branches to treat a patient.

13. A dental unit comprising:
at least one main water line for supplying a fluid drawn from a main water source;
a plurality of handpieces connected to the at least one main water line by a respective plurality of water supply lines, each handpiece being equipped with first means for shutting off a fluid supply from the respective water supply line to which it is connected;
at least one first independent branch flowing into the water supply lines, said at least one first branch connected to a source of at least one of a disinfectant liquid and sterilizing liquid;
means for selectively introducing the at least one of the disinfectant liquid and sterilizing liquid from the source into the water supply lines; and,
means for supplying a sterile fluid into and through the water supply lines to flush the at least one of the disinfectant liquid and sterilizing liquid out of the water supply lines.

14. The dental unit according to claim 13, wherein the means for supplying a sterile fluid comprises:
at least a second branch independent of the at least one main water line and independent of the water supply lines, said second branch flowing into the first branch to introduce the sterile fluid into the first branch and the water supply lines.

15. The dental unit according to claim 13, further comprising:
a first tank containing the at least one of the disinfectant liquid and sterilizing liquid connected to the first branch; and,
a second tank of sterile fluid that is selectively connected to the first branch in place of the first tank.

16. The dental unit according to claim 14, further comprising:
a tank containing the sterile fluid and positioned on the denial unit, said tank connected to the second branch.

17. The dental unit according to claim 16, wherein the tank is selectively removable from the dental unit and interchangeable.

18. The dental unit according to claim 14, further comprising:
a sub-branch of the second branch that flows into the at least one main water line upstream of the confluence between the first branch and the water supply lines, the sub-branch selectively introducing the sterile fluid in the water supply lines.

19. The dental unit according to claim 16, further comprising:
a sub-branch of the second branch that flows into the at least one main water line upstream of the confluence between the first branch and the water supply lines, the sub-branch selectively introducing the sterile fluid in the water supply lines.

20. The dental unit according to claim 18, further comprising:
a sub-branch of the second branch that flows into the at least one main water line upstream of the confluence between the first branch and the water supply lines, the sub-branch selectively introducing the sterile fluid in the water supply lines.

* * * * *